(12) United States Patent
Shanks et al.

(10) Patent No.: US 6,746,473 B2
(45) Date of Patent: Jun. 8, 2004

(54) THERAPEUTIC LASER DEVICE

(75) Inventors: Steven C. Shanks, Mesa, AZ (US); Kevin B. Tucek, Gilbert, AZ (US)

(73) Assignee: Erchonia Patent Holdings, LLC, Mesa, AZ (US)

( * ) Notice: Subject to any disclaimer, the term of this patent is extended or adjusted under 35 U.S.C. 154(b) by 0 days.

(21) Appl. No.: 09/932,907

(22) Filed: Aug. 20, 2001

(65) Prior Publication Data

US 2002/0123781 A1 Sep. 5, 2002

Related U.S. Application Data

(60) Provisional application No. 60/273,282, filed on Mar. 2, 2001.

(51) Int. Cl.[7] .............................................. A61N 5/067
(52) U.S. Cl. ............................................. 607/89; 606/9
(58) Field of Search .................. 607/88, 89; 606/9–13, 606/17

(56) References Cited

U.S. PATENT DOCUMENTS

| | | | |
|---|---|---|---|
| 4,905,690 A | | 3/1990 | Ohshiro et al. |
| 4,930,504 A | * | 6/1990 | Diamantopoulos et al. ... 607/88 |
| 5,649,924 A | | 7/1997 | Everett et al. |
| 5,655,547 A | | 8/1997 | Karni |
| 5,707,403 A | | 1/1998 | Grove |
| 5,755,752 A | | 5/1998 | Segal |
| 5,879,376 A | * | 3/1999 | Miller .......................... 607/89 |
| 5,954,710 A | | 9/1999 | Paolini et al. |
| 5,984,915 A | | 11/1999 | Loeb et al. |
| 6,013,096 A | | 1/2000 | Tucek |
| 6,063,108 A | * | 5/2000 | Salansky et al. ............... 607/89 |
| 6,074,411 A | | 6/2000 | Lai et al. |
| 6,106,516 A | | 8/2000 | Massengill |
| 6,110,195 A | * | 8/2000 | Xie et al. ...................... 607/89 |
| 6,176,854 B1 | | 1/2001 | Cone |
| 6,033,431 A1 | | 3/2001 | Segal |
| 6,206,873 B1 | | 3/2001 | Paolini et al. |
| 6,267,779 B1 | * | 7/2001 | Gerdes ......................... 607/89 |
| 6,273,885 B1 | * | 8/2001 | Koop et al. .................... 606/9 |
| 6,413,267 B1 | * | 7/2002 | Dumoulin-White et al. .. 607/89 |

* cited by examiner

Primary Examiner—Lee Cohen
Assistant Examiner—Henry M. Johnson
(74) Attorney, Agent, or Firm—Etherton Law Group, LLC; Sandra L. Etherton

(57) ABSTRACT

An improved hand-held laser device that can simultaneously provide multiple types of low level laser therapy treatments. The device enables laser light of different pulse widths, different beam shapes and spot sizes to be applied externally to a patient's body. The device includes multiple laser sources. In the preferred embodiment, two semiconductor diode laser sources simultaneously provide two separate laser beams, one laser beam producing a line of continuous red laser light and the other producing a spot of pulsed laser light.

13 Claims, 2 Drawing Sheets

THERAPEUTIC LASER DEVICE

CROSS-REFERENCE TO RELATED APPLICATIONS

This application claims the benefit of co-pending U.S. Provisional Application No. 60/273,282 filed Mar. 2, 2001.

FIELD OF INVENTION

This invention relates generally to medical devices that employ lasers. More particularly, this invention relates to an improved hand-held laser light generator device.

BACKGROUND

Low energy laser therapy (LLLT) is used in the treatment of a broad range of conditions. LLLT improves wound healing, reduces edema, and relieves pain of various etiologies, including successful application post-operatively to liposuction to reduce inflammation and pain. LLLT is also used during liposuction procedures to facilitate removal of fat by causing intracellular fat to be released into the interstice. It is also used in the treatment and repair of injured muscles and tendons.

LLLT utilizes low level laser energy, that is, the treatment has a dose rate that causes no immediate detectable temperature rise of the treated tissue and no macroscopically visible changes in tissue structure. Consequently, the treated and surrounding tissue is not heated and is not damaged. There are a number of variables in laser therapy including the wavelength of the laser beam, the area impinged by the laser beam, laser energy, pulse width, treatment duration and tissue characteristics. The success of each therapy depends on the relationship and combination of these variables. For example, liposuction may be facilitated with one regimen utilizing a given wavelength and treatment duration, whereas pain may be treated with a regimen utilizing a different wavelength and treatment duration, and inflammation a third regimen. Specific devices are known in the art for each type of therapy.

Often it is desirable to treat a patient for multiple types of problems during a single treatment. Because specific therapies require different regimen, treating multiple problems currently requires multiple laser devices. It is desirable to provide a device that enables multiple types of treatments with a single device. It is also desirable to be able to provide multiple treatments simultaneously with a single device.

Therefore, an object of this invention is to provide a laser therapy device that enables multiple types of treatments. It is another object to provide a single device that provides these treatments simultaneously. It is another object of this invention to provide an apparatus that can simultaneously emit multiple beams of laser light. It is another object of this invention to provide an apparatus that can simultaneously emit laser light in multiple different pulse widths. It is a further object of this invention to provide an apparatus that can simultaneously emit laser light in multiple beam shapes and spot sizes. It is a particular object of this invention to provide a hand-held therapeutic laser device to provide low level laser therapy which can be used to simultaneously facilitate liposuction, treat post-operative inflammation, and post-operative pain.

SUMMARY OF THE INVENTION

This invention is an improved hand-held laser device that can simultaneously provide multiple types of low level laser therapy treatments. The device enables laser light of different pulse widths, different beam shapes and spot sizes to be applied externally to a patient's body. The device includes multiple laser sources. In the preferred embodiment, two semiconductor diode laser sources simultaneously provide two separate laser beams, one laser beam producing a line of continuous red laser light and the other producing a spot of pulsed laser light.

DETAILED DESCRIPTION OF THE INVENTION

Figure 1:
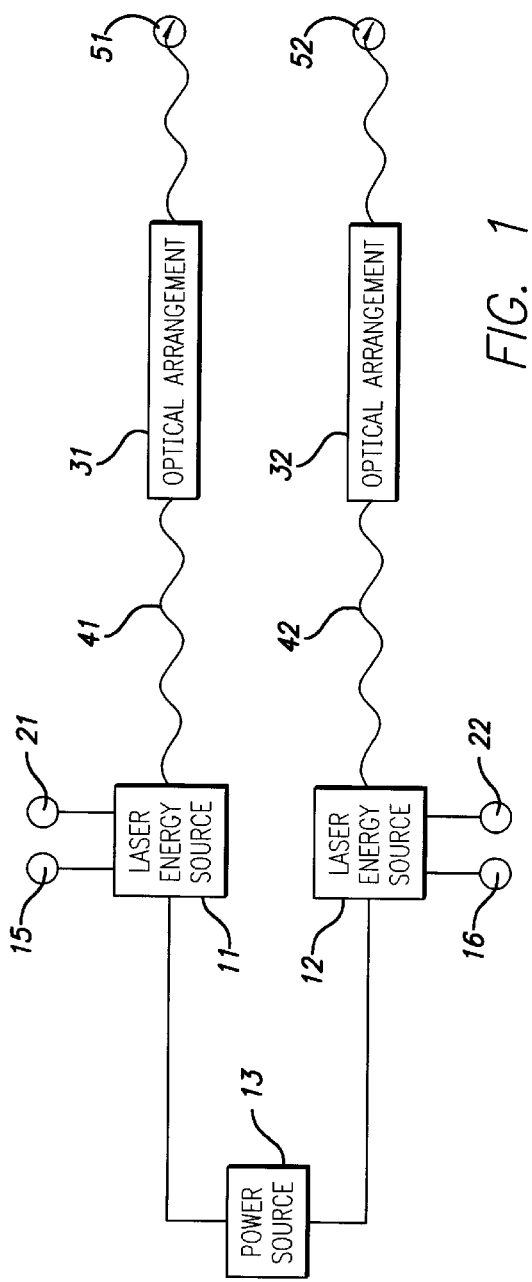
FIG. 1 is an electrical schematic illustration of a preferred embodiment of the present invention.

Referring to the drawings, there is illustrated a hand-held laser device designated. The device includes a plurality of laser energy sources, a power source, an optical arrangement, a wand, and a control circuit.

FIG. 1 shows the preferred embodiment in which a first laser energy source 11 and a second energy source 12 are connected to a power source 13. The power source preferably provides direct current, such as that provided by a battery, but may instead provide alternating current such as that provided by conventional building current that is then converted to direct current. Separate control means 15, 16 are connected to the laser energy sources 11, 12 respectively and act as on/off switches to control the period of time the laser light is generated. These laser energy sources can be energized independently or simultaneously which, throughout this specification, refers to acts occurring at generally at the same time.

Laser energy sources are known in the art for use in low-level laser therapy. They include Helium-Neon lasers having a 632 nm wavelength and semiconductor diode lasers with a broad range of wavelengths between 600–800 nm. The laser energy sources in the preferred embodiment are two semiconductor laser diodes that produce light in the red range of the visible spectrum, having wavelengths of about 635 nm. Other suitable wavelength are used for other particular applications. While many LLLT regimens include visible laser light, it is advantageous to utilize at least one laser beam in the visible/UV energy spectrum so that the operator can see the laser light as it impinges the patent's body and the area treated can be easily defined. Solid state and tunable semiconductor laser diodes may also be employed to achieve the desired wavelength.

Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen.

Control means 21, 22 are connected to the laser energy sources 11, 12, respectively, to form a control circuit that control the duration of each pulse of laser light emitted, referred to herein as the pulse width. When there are no pulses, a continuous beam of laser light is generated. Pulse widths of at least one-millionth of a second may be employed to achieve the desired effect on the patient's tissue. The goal of LLLT regimen is to deliver laser energy to the targeted tissue utilizing a pulse width short enough to sufficiently energize the targeted tissue and avoid thermal damage to adjacent tissue.

Each laser beam 41, 42 exits the laser and is shone through optical arrangements 31, 32, respectively, that produce beam spots 51, 52 respectively of certain shapes. The beam spot is the cross-sectional shape and size of the emitted beam as it exits the optical arrangement. For example, a laser beam of circular cross-section creates a circular beam spot as the laser light impinges the patient's skin. If the laser light emitted is in the visible range, a circular spot can be seen on the patient's skin of substantially the same diameter as the laser beam emitted from the optics arrangement. In the preferred embodiment, the first laser beam is passed through an optical arrangement that generates a beam of substantially linear cross-section, resulting in a line of laser light seen on the patient's skin. The second laser passes through an optical arrangement that generates a beam of circular cross-section, resulting in a circular spot shape as seen on the patient's skin.

Figure 2:
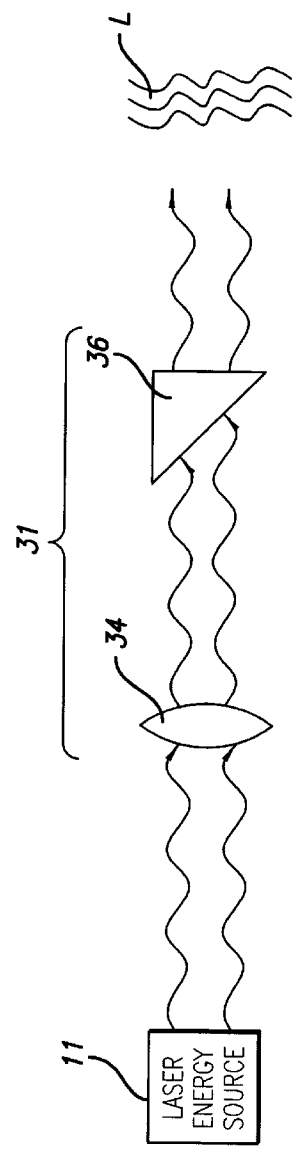
FIG. 2 is a schematic view of the optical arrangement of the linear spot shape of the preferred embodiment.

As shown in FIG. 2 the first optical arrangement 31 of the preferred device includes a collimating lens 34 and a line generating prism 36. The collimating lens 34 and the line generating prism 36 are disposed in serial relation to the laser energy source 11. The collimating lens 34 and the line generating prism 36 receive and transform the generated beam of laser light into the line of laser light L. As an alternative, a suitable electrical or mechanical arrangement could be substituted for the optical arrangement 31.

Figure 3:
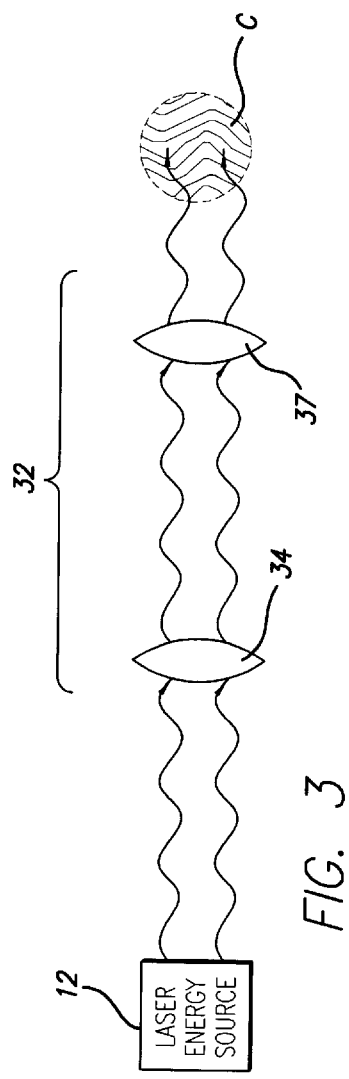
FIG. 3 is a schematic view of the optical arrangement of the circular spot shape of the preferred embodiment.

As shown in FIG. 3 the second optical arrangement 32 of the preferred device includes a collimating lens 34 and a beam spot shaping lens 37. As with the first optical arrangement, the collimating lens 34 and beam spot shaping lens 37 are disposed in serial relation to the laser energy source 12. The collimating lens 34 and beam spot shaping lens 37 receive and transform the generated beam of laser light into a circular beam spot of laser light C. As an alternative, a suitable electrical or mechanical arrangement could be substituted for the optical arrangement 32 to achieve a desired spot shape.

The device may utilize as many lasers and optical arrangements as necessary to obtain the desired emissions and spot shapes. For example, the device may employ two laser diodes each with a collimating lens, such that two substantially circular spot shapes are achieved. Or, for example, the device may employ two laser diodes each with an optical arrangement such that two substantially linear spot shapes are achieved. Or, in another example, more than two lasers may be used and optical arrangements aligned such that two or more of the laser beams have substantially similar spot shapes and are co-incident where they impinge the patient's skin.

Figure 4:
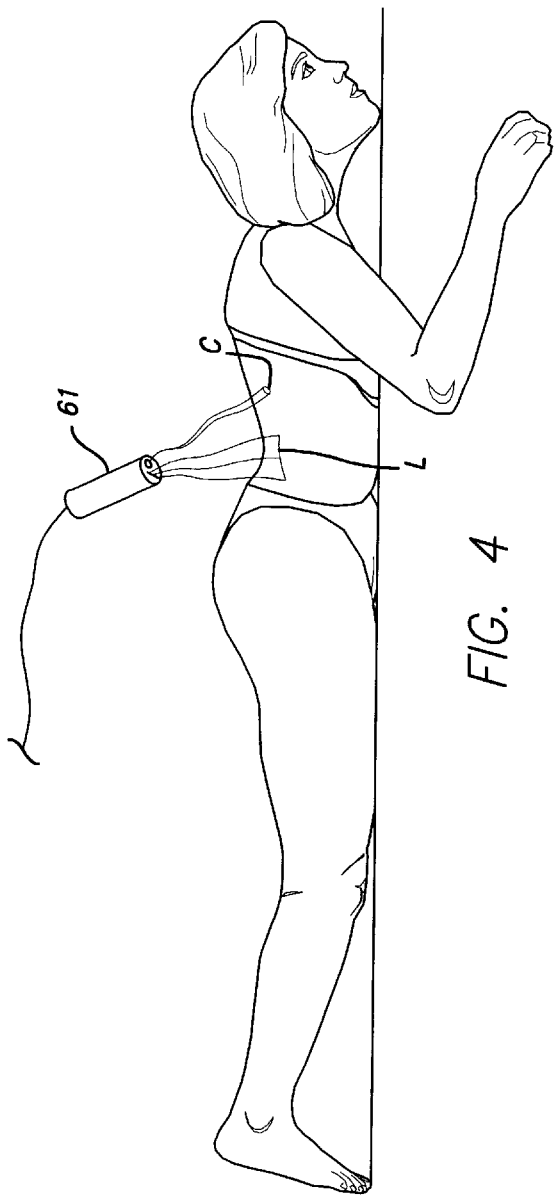
FIG. 4 is a schematic illustration of application of low-level laser radiation using the preferred embodiment of the present invention.

In order to direct the laser light to the desired area on a patient, the laser light is emitted from a lightweight, handheld pointer referred to herein as a wand 61. See FIG. 4. The wand 61 is preferably an elongated hollow tube defining an interior cavity which is shaped to be easily retained in a user's hand. In the preferred embodiment the laser energy sources 11, 12 are mounted in the wand's interior cavity, although the laser energy sources could be remotely located and the laser light conducted by fiber optics to the wand. The wand may take on any shape that enables the laser light to be directed as needed such as tubular, T-shaped, substantially spherical, or rectangular (like a television remote control device).

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A laser device comprising:
   a) a plurality of laser energy sources for generating a plurality of laser beams;
   b) a wand from which the laser beams emit, the wand housing the laser energy sources within and being capable of being retained in a hand of a user and freely moved relative to the surface of the skin of a patient; and
   c) an optical arrangement attached to the wand for receiving the laser beams and for transforming each of the laser beams into a desired spot shape.

2. A device according to claim 1 wherein at least two of the laser beams are emitted simultaneously.

3. A device according to claim 1 further comprising a controller for independently controlling the generation of laser energy by each of the plurality of laser energy sources.

4. A device according to claim 1 wherein each of the laser energy sources is less than one watt.

5. A device according to claim 1 wherein at least one of the laser energy sources is a semiconductor diode.

6. A device according to claim 5 wherein the laser energy source in claim 5 generates a laser beam having a wavelength in the visible range.

7. A device according to claim 1 wherein at least one of the spot shapes is substantially linear.

8. A device according to claim 1 further comprising a first laser beam having a first spot shape and a second laser beam having a second spot shape wherein the first spot shape is substantially linear and the second spot shape is circular.

9. A device according to claim 1 further comprising a control circuit for controlling a pulse width of each laser beam.

10. A device according to claim 9 wherein the pulse width of at least one of the laser beams is such that the laser light emitted is substantially continuous.

11. A device according to claim 9 further comprising a first laser beam having a first pulse width and a second laser beam having a second pulse width wherein the first pulse width is such that the laser light emitted is substantially continuous and the second pulse width is not zero.

12. A device according to claim 11 wherein the second pulse width is at least one-millionth of a second.

13. A therapeutic laser device comprising:
   a) a first semiconductor diode laser energy source generating a first laser beam having a first pulse width and a second semiconductor diode laser energy source generating a second laser beam having a second pulse width, wherein at least one of the laser beams has a wavelength in the red range of the visible spectrum;
   b) a wand from which the laser beams emit, the wand having an interior cavity that houses the laser energy sources and that is capable of being retained in a hand of a user and freely moved relative to the surface of the skin of a patient;

c) an optical arrangement mounted in the interior cavity of the wand for receiving the laser beams and for transforming each of the laser beams into a desired spot shape wherein the first laser beam's spot shape is substantially linear and the second laser beam's spot shape is substantially circular;

d) a control circuit for controlling the first pulse width and the second pulse width wherein the first pulse width is a continuous emission and the pulse width is greater than zero.

* * * * *